(12) United States Patent
Seo (10) Patent No.: US 10,485,709 B2
(45) Date of Patent: Nov. 26, 2019

(54) ROTARY ASPIRATOR

(71) Applicant: Dong Jin Seo, Incheon (KR)

(72) Inventor: Dong Jin Seo, Incheon (KR)

( * ) Notice: Subject to any disclaimer, the term of this patent is extended or adjusted under 35 U.S.C. 154(b) by 377 days.

(21) Appl. No.: 15/500,857

(22) PCT Filed: Jul. 31, 2015

(86) PCT No.: PCT/KR2015/008048
§ 371 (c)(1),
(2) Date: Jan. 31, 2017

(87) PCT Pub. No.: WO2016/018122
PCT Pub. Date: Feb. 4, 2016

(65) Prior Publication Data
US 2017/0216104 A1     Aug. 3, 2017

(30) Foreign Application Priority Data

Aug. 1, 2014 (KR) .................. 10-2014-0098828

(51) Int. Cl.
*A61B 5/00* (2006.01)
*A61F 13/38* (2006.01)
*A61F 13/12* (2006.01)

(52) U.S. Cl.
CPC ............ *A61F 13/38* (2013.01); *A61F 13/126* (2013.01)

(58) Field of Classification Search
CPC ........ A61B 17/320708; A61B 10/0291; A61B 10/02; A61B 17/50; A61B 1/303; A61B 2017/0023; A61B 2017/320008; A61B 18/1482; A61B 2017/4225; A61F 11/006; A61F 11/00; A61F 13/38

USPC ............... 600/300, 301, 569, 570, 572, 581; 606/160, 162; 604/514
See application file for complete search history.

(56) References Cited

U.S. PATENT DOCUMENTS 4,620,548 A * 11/1986 Hasselbrack ...... A61B 10/0291
                                                        600/571
4,788,985 A * 12/1988 Manning ................ A61B 10/02
                                                        600/569
4,800,896 A *  1/1989 Jalowayski ............ A61B 10/04
                                                        600/572

(Continued)

FOREIGN PATENT DOCUMENTS

CN      202051991 U    11/2011
JP        3011688 U     3/1995

(Continued)

*Primary Examiner* — May A Abouelela
(74) *Attorney, Agent, or Firm* — Novick, Kim & Lee, PLLC; Sang Ho Lee (57) ABSTRACT

A rotary aspirator according to the present invention includes: a body portion which has a length in a front and rear direction, and has an outer circumferential surface formed as any one of a circular shape, an elliptical shape, and a polygonal shape in a lateral direction; a handle which is connected to a rear end of the body portion and has a smaller diameter than the rear end of the body portion so that a user moves the handle forward and rearward and rotates the handle in a state in which the user holds the handle by hand; and an absorbing member which is continuously and spirally wound in the front and rear direction of the body portion and absorbs nasal mucus of a target person.

9 Claims, 7 Drawing Sheets

(56) References Cited

U.S. PATENT DOCUMENTS

| | | | | | |
|---|---|---|---|---|---|
| 4,877,037 | A | * | 10/1989 | Ko | A61B 10/0291 600/569 |
| 5,078,968 | A | * | 1/1992 | Nason | A61B 10/02 422/411 |
| 5,084,005 | A | * | 1/1992 | Kachigian | A61B 10/02 600/569 |
| 5,121,752 | A | * | 6/1992 | Canna | A61B 10/0291 600/572 |
| 5,238,649 | A | * | 8/1993 | Nason | A61B 10/02 422/411 |
| 5,334,212 | A | * | 8/1994 | Karell | A61B 1/227 128/864 |
| 5,623,942 | A | * | 4/1997 | Pestes | A61B 10/02 600/562 |
| 5,725,481 | A | * | 3/1998 | Buck | A61B 10/0291 600/572 |
| 5,735,808 | A | * | 4/1998 | Delgado | A61F 13/38 15/210.1 |
| 5,968,062 | A | * | 10/1999 | Thomas | A61B 17/1615 606/160 |
| 6,033,417 | A | * | 3/2000 | Tseng | A61F 11/006 606/106 |
| 6,074,405 | A | * | 6/2000 | Koch | A61B 17/50 606/160 |
| 6,080,126 | A | * | 6/2000 | Zygmont | A61F 13/38 600/569 |
| 6,695,802 | B1 | * | 2/2004 | Thompson | A61F 11/006 604/1 |
| 6,723,057 | B1 | * | 4/2004 | Pearce | A61B 10/0291 600/562 |
| 7,749,173 | B2 | * | 7/2010 | Larkin | A61B 10/02 600/562 |
| 8,439,847 | B2 | * | 5/2013 | Larkin | A61B 10/02 600/562 |
| 9,033,897 | B2 | * | 5/2015 | Benabid | A61B 10/02 600/562 |
| 2002/0004664 | A1 | * | 1/2002 | Gerstein | A61F 11/006 606/162 |
| 2002/0120214 | A1 | * | 8/2002 | Cole | A61B 10/0291 600/570 |
| 2002/0123697 | A1 | * | 9/2002 | Ishizaka | A61B 10/0045 600/572 |
| 2006/0161076 | A1 | * | 7/2006 | Gombrich | A61B 10/00 600/569 |
| 2007/0142746 | A1 | * | 6/2007 | Scampini | A61B 10/0045 600/572 |
| 2007/0167900 | A1 | * | 7/2007 | Kanjilal | A61B 10/0038 604/1 |
| 2007/0249961 | A1 | * | 10/2007 | Morrison | A61B 10/0045 600/572 |
| 2011/0004122 | A1 | * | 1/2011 | Sangha | A61B 10/0045 600/572 |
| 2013/0184684 | A1 | * | 7/2013 | Yardley | A61F 13/126 604/514 |
| 2013/0231588 | A1 | * | 9/2013 | Fukuhara | A61B 10/0275 600/572 |
| 2014/0066807 | A1 | * | 3/2014 | Lundkvist | A61B 10/0096 600/572 |
| 2014/0073989 | A1 | * | 3/2014 | Vom | A61B 10/0291 600/572 |
| 2015/0018861 | A1 | * | 1/2015 | Olson | A61F 11/006 606/162 |
| 2015/0142029 | A1 | * | 5/2015 | Fahn | A61F 11/006 606/162 |
| 2015/0297196 | A1 | * | 10/2015 | Ching | A61B 10/0045 206/223 |

FOREIGN PATENT DOCUMENTS

| | | |
|---|---|---|
| JP | H1057269 A | 3/1998 |
| JP | 2001327528 A | 11/2001 |
| JP | 2006-136699 A | 6/2006 |
| JP | 2007029661 A | 2/2007 |
| JP | 2012-152329 A | 8/2012 |
| KR | 20-0210862 Y1 | 1/2001 |
| KR | 20-0284743 Y1 | 8/2002 |
| KR | 20-0436518 Y1 | 8/2007 |
| KR | 20-0443746 Y1 | 3/2009 |
| KR | 20-2011-0006452 U | 6/2011 |

\* cited by examiner

ROTARY ASPIRATOR

TECHNICAL FIELD

The present invention relates to a rotary aspirator, and more particularly, to a rotary aspirator which removes nasal mucus from a target person by continuously and spirally winding and coupling a nasal mucus absorbing member around an outer circumference of a body portion, and pushing or pulling, and rotating the body portion, such that because artificial suction force is not used, it is possible to remove the nasal mucus without irritation, and to prevent the occurrence of injuries to a mucous membrane and a blood vessel inside the nose.

BACKGROUND ART

In general, it is difficult for an infant or a patient, who cannot smoothly move, to remove nasal mucus by him/herself even though he/she suffers from nasal obstruction caused by the nasal mucus, and severe nasal obstruction may cause a respiratory disorder, which causes a dangerous situation.

As such, because it is difficult for an infant or a patient to remove the nasal mucus by him/herself, a nasal aspirator, which may artificially remove the nasal mucus existing in the nose, is widely used.

In most instances, the nasal aspirator in the related art uses a method of forcedly sucking air, and includes a suction device which may suck the air, and a suction nozzle which is inserted into a nose of a target person by a predetermined length in a state in which the suction nozzle is connected to the suction device.

However, because the nasal aspirator in the related art uses the method of forcedly sucking air, there are various problems in that the nasal aspirator may damage a nasal mucous membrane or a blood vessel, and thus the blood vessel is injured, or nasal bleeding occurs.

Therefore, there is a need for an aspirator capable of gently removing nasal mucus without causing injuries to the nasal mucous membrane or the blood vessel.

As literature associated with the present invention, there is Korean Utility Model Registration No. 20-0436518 (Aug. 24, 2007) that discloses a nasal aspirator.

DISCLOSURE

Technical Problem

An object of the present invention is to provide a rotary aspirator which removes nasal mucus from a target person by continuously and spirally winding and coupling a nasal mucus absorbing member around an outer circumference of a body portion, and pushing or pulling, and rotating the body portion, such that because artificial suction force is not used, it is possible to remove the nasal mucus without irritation, and to prevent the occurrence of injuries to a mucous membrane and a blood vessel inside the nose.

Technical Solution

A rotary aspirator according to the present invention includes: a body portion which has a length in a front and rear direction, and has an outer circumferential surface formed as any one of a circular shape, an elliptical shape, and a polygonal shape in a lateral direction; a handle which is connected to a rear end of the body portion and has a smaller diameter than the rear end of the body portion so that a user moves the handle forward and rearward and rotates the handle in a state in which the user holds the handle by hand; and an absorbing member which is continuously and spirally wound in the front and rear direction of the body portion and absorbs nasal mucus of a target person.

In addition, a front end of the body portion may be formed to protrude in a hemispheric or elliptical shape.

In addition, a coupling hole into which one end or both ends of the absorbing member is/are inserted may be penetratively formed in the body portion in a lateral direction.

In addition, the coupling hole may be opened to a front side of the body portion so that the absorbing member is coupled through the front side of the body portion.

In addition, the coupling hole may be formed to have a width narrower than the absorbing member, and may hold an outer surface of the absorbing member.

In addition, a catching protrusion for catching and positioning the absorbing member may be formed to protrude on an outer surface of the body portion in a longitudinal direction.

In addition, a catching protrusion or a catching groove for catching and positioning the absorbing member may be concavely formed at an upper surface or a lower surface of the coupling hole.

In addition, the absorbing member may be attached to the outer circumferential surface of the body portion by an adhesive.

In addition, a diameter of the body portion may be gradually decreased forward.

Advantageous Effects

According to the present invention, the nasal mucus is removed from the target person by continuously and spirally winding and coupling the nasal mucus absorbing member around the outer circumference of the body portion, and pushing or pulling, and rotating the body portion, and as a result, because artificial suction force is not used, it is possible to remove the nasal mucus without irritation, and to prevent the occurrence of injuries to a mucous membrane and a blood vessel inside the nose.

Further, the rotary aspirator may minimize the occurrence of injuries to a mucous membrane inside the nose, a blood vessel, or a periphery of a nostril because the rotary aspirator uses surface viscosity of nasal mucus, the rotary aspirator is environmentally friendly because a separate power source is not used, and the rotary aspirator may be used semipermanently because the absorbing member 300 may be changed and used.

DESCRIPTION OF MAIN REFERENCE NUMERALS OF DRAWINGS

100: body portion
110: coupling hole
120: front end
130: stepped portion
200: handle
300: absorbing member
400, 400': catching protrusion

BEST MODE

Hereinafter, exemplary embodiments of the present invention will be described in detail with reference to the accompanying drawings.

Advantages and features of the present invention and methods of achieving the advantages and features will be clear with reference to exemplary embodiments described in detail below together with the accompanying drawings.

However, the present invention is not limited to the exemplary embodiments disclosed herein but will be implemented in various forms. The exemplary embodiments are provided so that the present invention is completely disclosed, and a person of ordinary skilled in the art can fully understand the scope of the present invention. Therefore, the present invention will be defined only by the scope of the appended claims.

In addition, in the description of the present invention, a detailed explanation of publicly known related technologies may be omitted so as to avoid unnecessarily obscuring the subject matter of the present invention.

Figure 1:
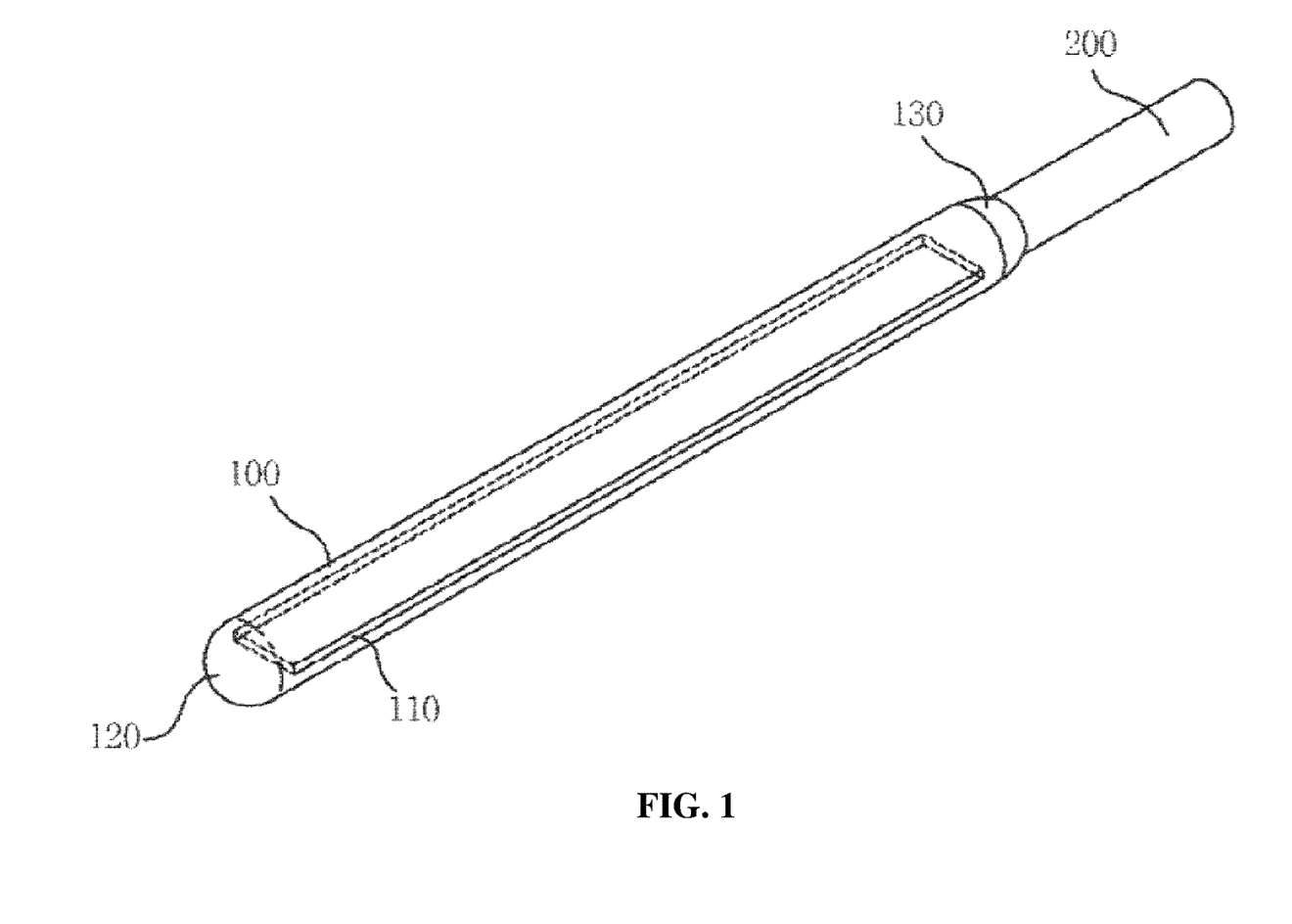
FIG. 1 is a perspective view illustrating a rotary aspirator according to the present invention.
Figure 2:
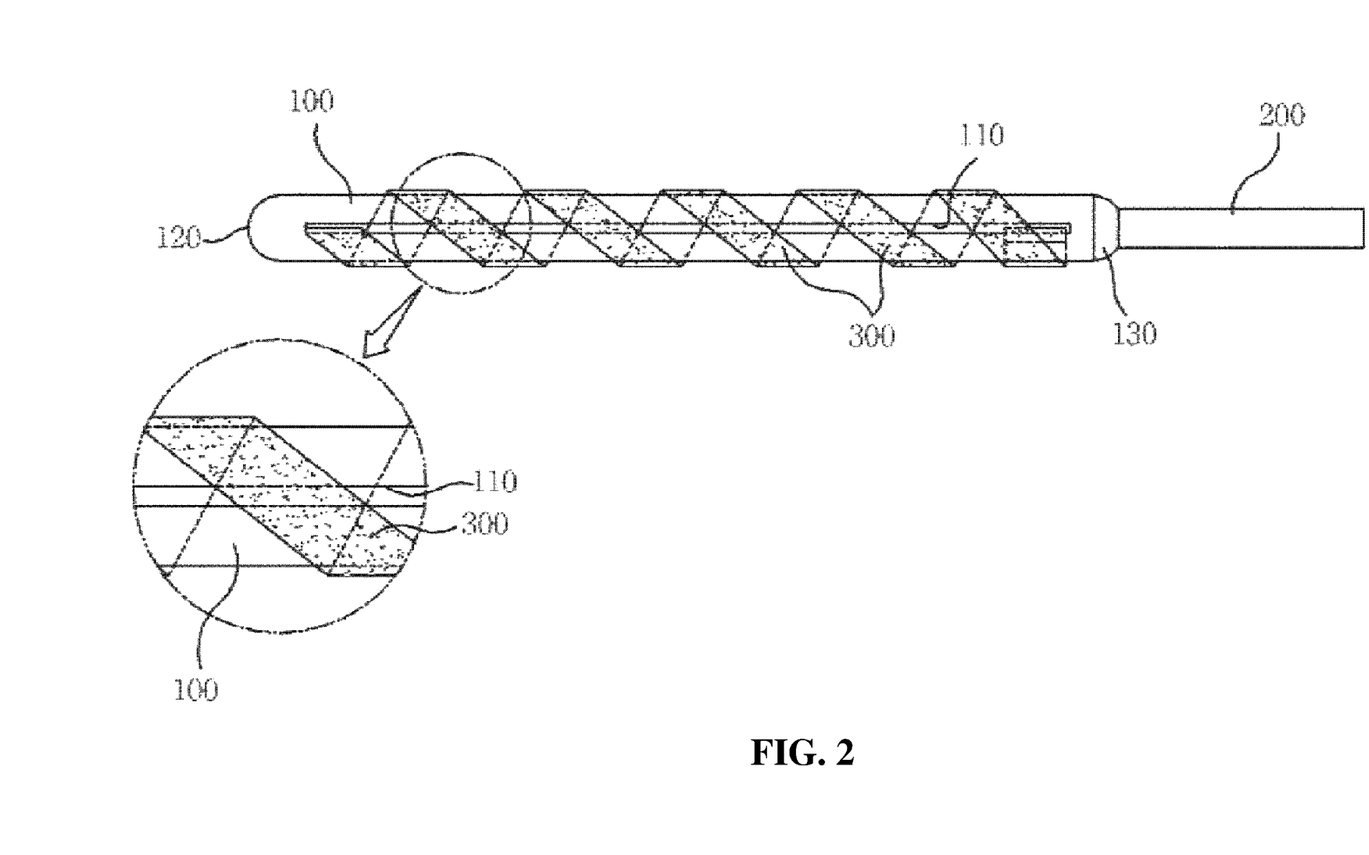
FIG. 2 is a side view illustrating the rotary aspirator according to the present invention.

FIG. 1 is a perspective view illustrating a rotary aspirator according to the present invention, and FIG. 2 is a side view illustrating the rotary aspirator according to the present invention.

Figure 3:
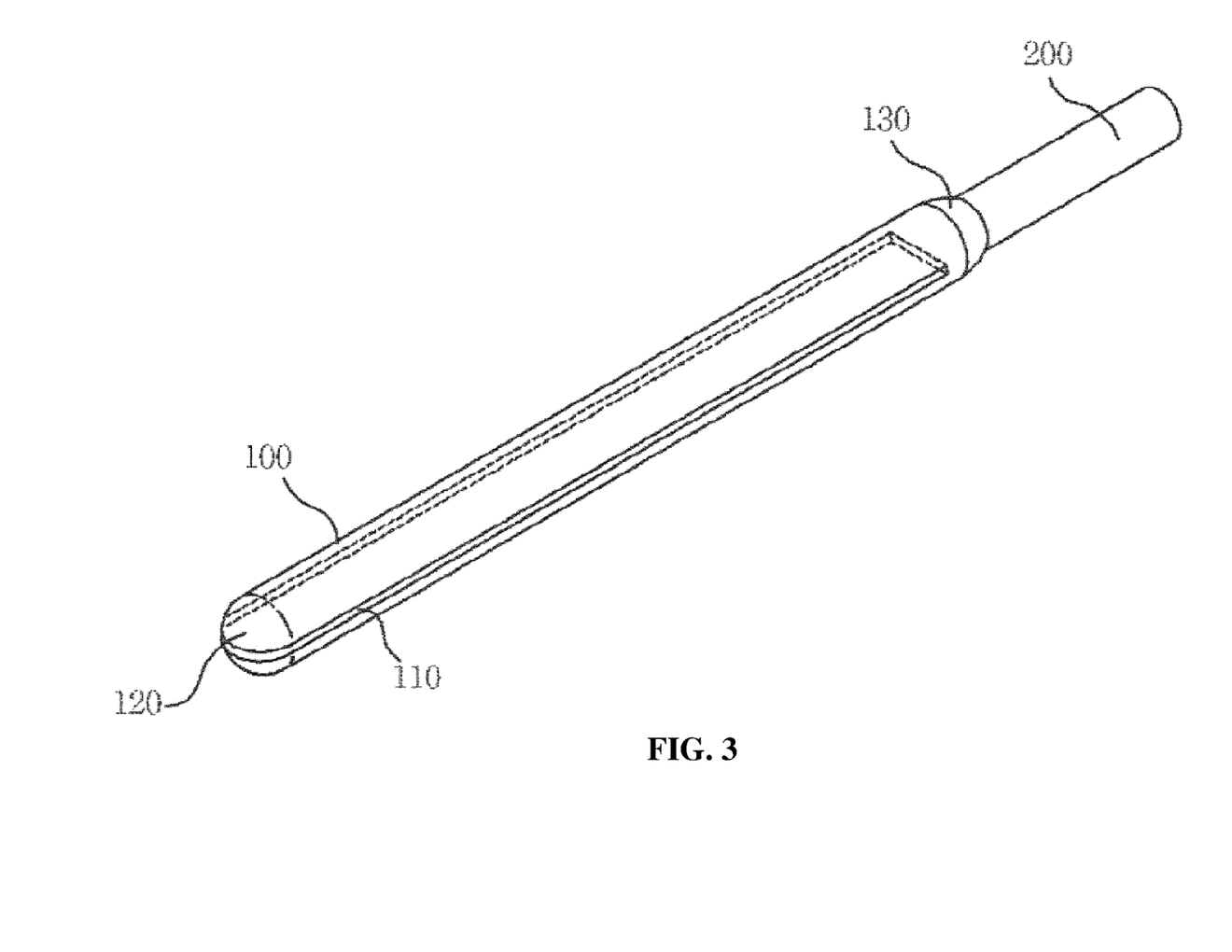
FIG. 3 is a perspective view illustrating a state in which a coupling hole is opened toward a front side of a body portion of the rotary aspirator according to the present invention.

Further, FIG. 3 is a perspective view illustrating a state in which a coupling hole is opened toward a front side of a body portion of the rotary aspirator according to the present invention.

Figure 4:
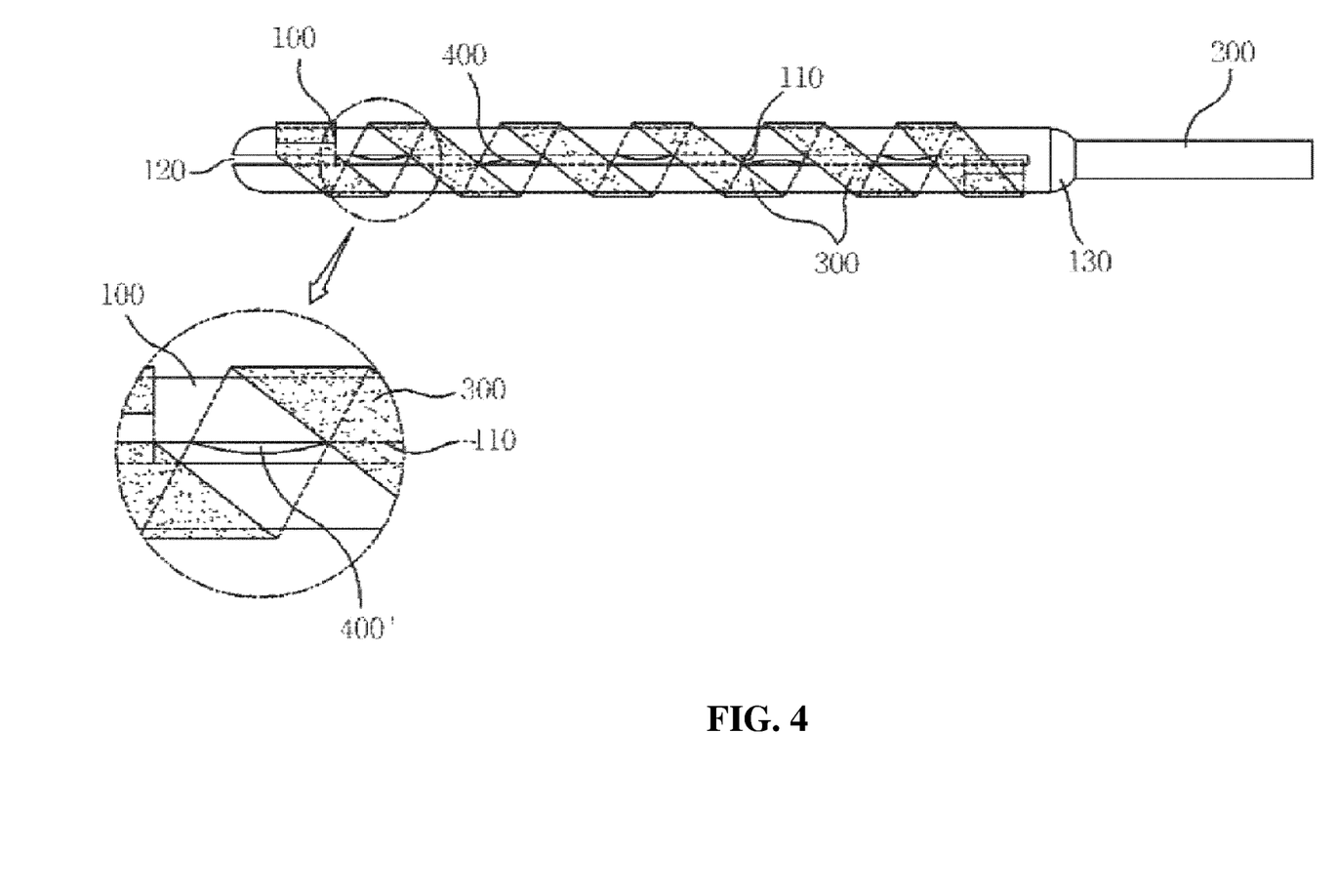
FIG. 4 is a side view illustrating a state in which the coupling hole is opened toward the front side of the body portion of the rotary aspirator according to the present invention.
Figure 5:
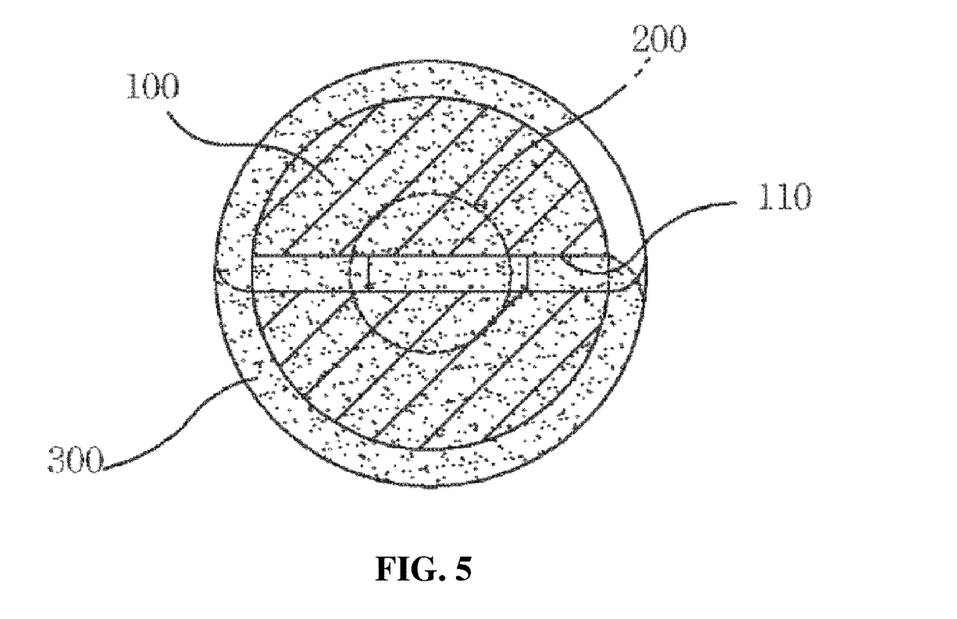
FIG. 5 is a cross-sectional view illustrating the rotary aspirator according to the present invention.

Further, FIG. 4 is a side view illustrating a state in which the coupling hole is opened toward the front side of the body portion of the rotary aspirator according to the present invention, and FIG. 5 is a cross-sectional view illustrating the rotary aspirator according to the present invention.

Figure 6:
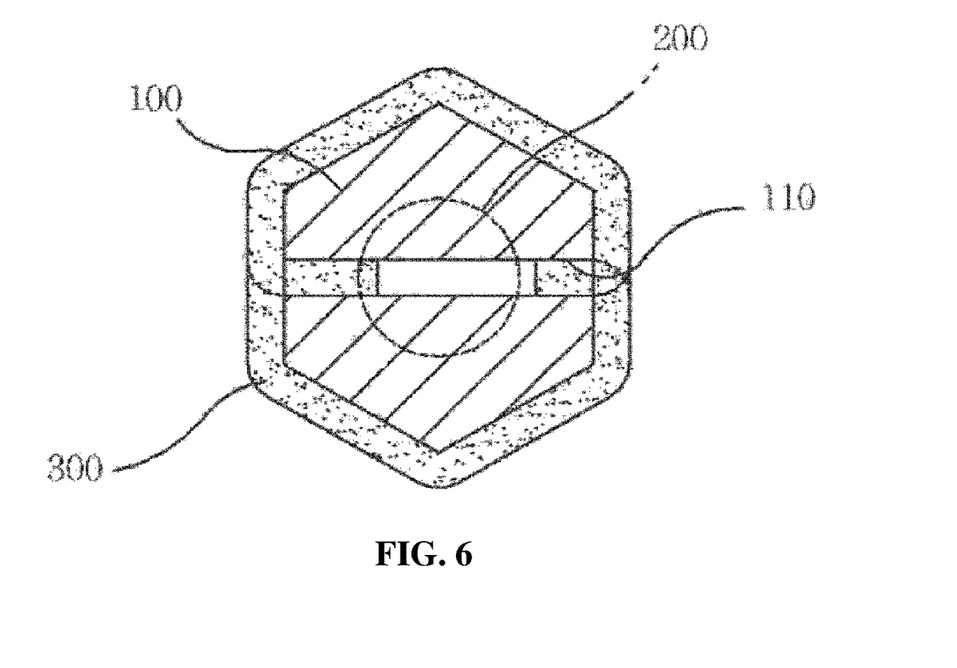
FIG. 6 is a cross-sectional view illustrating a state in which the rotary aspirator according to the present invention has a polygonal shape.

In addition, FIG. 6 is a cross-sectional view illustrating a state in which the rotary aspirator according to the present invention has a polygonal shape.

As illustrated in FIGS. 1 to 7, the rotary aspirator according to the present invention includes a body portion 100, a handle 200, and an absorbing member 300.

First, the body portion 100 has a predetermined length in a front and rear direction, and an outer circumferential surface of the body portion 100 may be formed as a circular shape, a curved shape, a polygonal shape, or the like in a lateral direction.

Here, the body portion 100 may be manufactured by using any one of wood, synthetic resin, and metal, and may be manufactured by selectively using various materials as necessary.

Further, as illustrated in FIG. 1, the body portion 100 is illustrated in the form of a straight line, but the body portion 100 may be formed in the form of a curved line corresponding to a human body.

In addition, the body portion 100 may have an appropriate diameter and an appropriate length so as to be inserted into a nose of an infant or a patient who acts unnaturally.

Further, a front end 120 of the body portion 100 may be formed to have a horizontal surface as illustrated in FIG. 1, but may be formed to protrude in a hemispheric or elliptical shape as illustrated in FIGS. 3 and 4.

In particular, a coupling hole 110 into which one end or both ends of the absorbing member 300 to be described below is/are inserted may be penetratively formed in the body portion 100 in a lateral direction.

The coupling hole 110 has a shape cut out, in the form of a slit, in the body portion 100, and as a result, it is possible to hold an outer surface of the absorbing member 300 to be described below in two directions.

Further, the coupling hole 110 may be opened to a front side of the body portion 100 so that the absorbing member 300 to be described below may be coupled through the front side of the body portion 100.

In addition, the coupling hole 110 is formed to have a width narrower than the absorbing member 300, and may hold the outer surface of the absorbing member 300.

Figure 7:
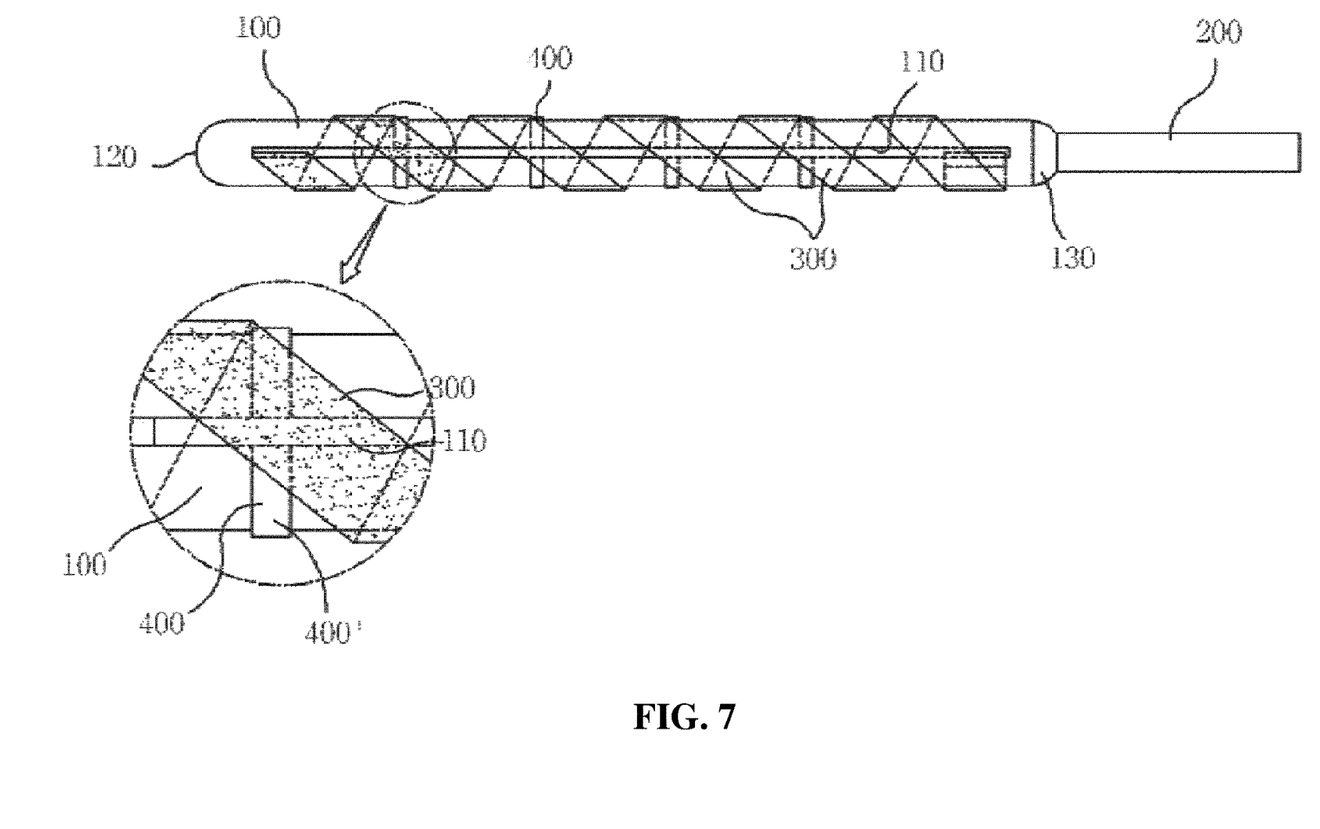
FIG. 7 is a cross-sectional view illustrating a state in which a catching protrusion is applied to the body portion of the rotary aspirator according to the present invention.

Meanwhile, catching protrusions 400 for catching and positioning the absorbing member 300 may be formed to protrude on the outer surface of the body portion 100 in a longitudinal direction.

A plurality of catching protrusions 400 may be formed in the front and rear direction of the body portion 100, and the catching protrusions 400 may be disposed to be spaced apart from each other.

In addition, catching protrusions 400' or catching grooves for catching and positioning the absorbing member 300 to be described below may be concavely formed at an upper surface or a lower surface of the coupling hole 110.

The catching protrusions 400' or the catching grooves serve to hold an outer circumferential surface of the absorbing member 300 to be described below with high frictional force.

Therefore, the catching protrusions 400' or the catching grooves may prevent the absorbing member 300 from being pushed and moved forward or rearward when the body portion 100 moves forward and rearward.

Meanwhile, although not illustrated, the body portion 100 may be manufactured in the form of a taper so that a diameter of the body portion 100 is gradually decreased forward.

That is, since the front side of the body portion 100 has a small diameter, it is possible to easily insert the body portion 100 into the nose of a target person.

Figure 8:
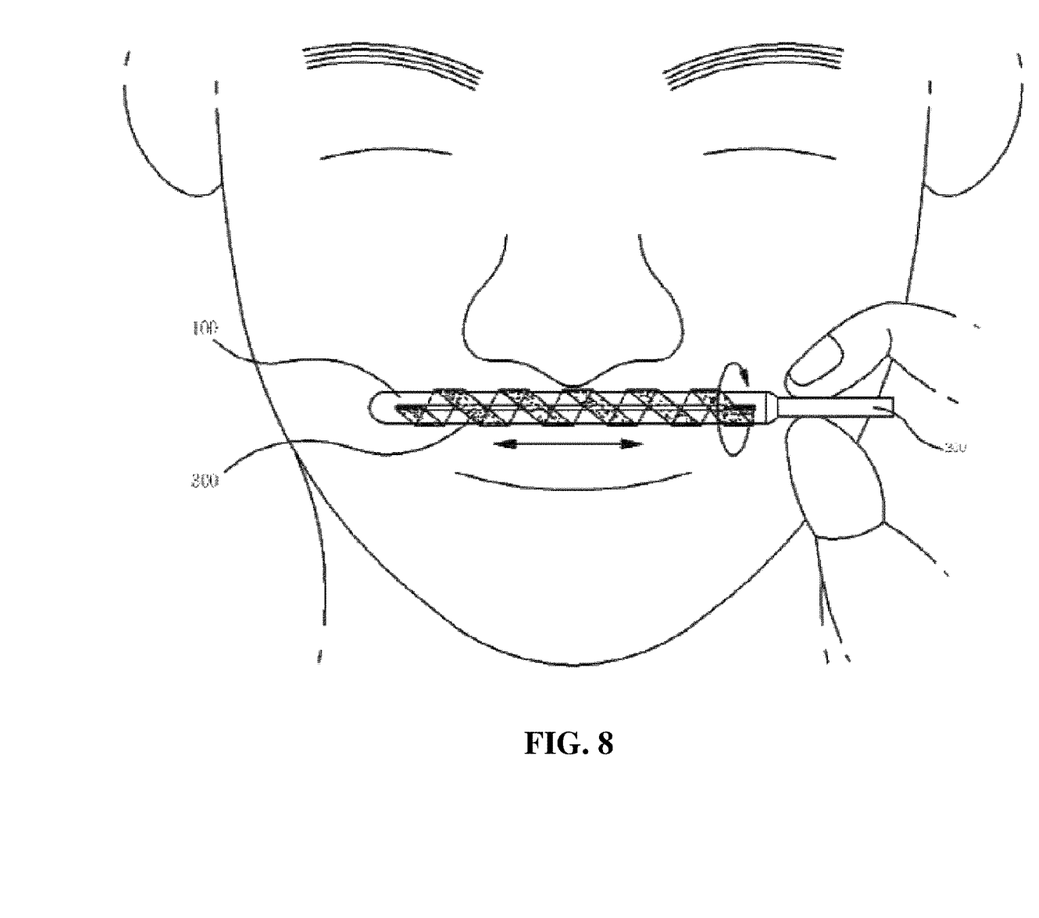
FIG. 8 is a view illustrating a state in which the rotary aspirator according to the present invention is used.

The handle 200 is connected to a rear end of the body portion and has a smaller diameter than the rear end of the body portion so that a user may move the handle 200 leftward and rightward and rotate the handle in a state in which the user holds the handle 200 by hand as illustrated in FIG. 8.

In this case, a stepped portion 130 may be formed at a connection portion between the handle 200 and the body portion 100 because of a difference in diameter.

Further, the handle 200 may be made of the same material as the body portion 100, but may be made of a material different from a material of the body portion 100 as necessary.

For example, an outer circumferential surface of the handle 200 may be coated with rubber, synthetic resin, or the like for preventing a slip, or a slit or the like for preventing a slip may be formed in the outer circumferential surface of the handle 200.

The absorbing member 300 is continuously and spirally wound in the front and rear direction of the body portion 100, and absorbs nasal mucus of the target person.

Here, the absorbing member 300 has a shape cut to a predetermined length, and may be coupled in such a manner as one end or both ends of the absorbing member 300 is/are inserted into the coupling hole 110.

Of course, the absorbing member 300 may be wound around the outer circumferential surface of the body portion 100 while continuously passing through the coupling hole 110.

In this case, the absorbing member 300 is held, with predetermined force, by both surfaces of the coupling hole 110, and as a result, a position of the absorbing member 300 may be stably maintained without being moved in the front and rear direction of the body portion 100 in use.

Further, any one of tissue, cotton, non-woven fabric, and fabric may be used as the absorbing member 300, but any material may be used as long as the material may absorb the nasal mucus.

In addition, the absorbing member 300 may be attached to the outer circumferential surface of the body portion 100 by an adhesive (not illustrated). Here, the adhesive may be made of a material harmless to humans.

The absorbing member 300 absorbs the nasal mucus by using viscosity of the nasal mucus and maximizing friction, and may remove the nasal mucus in such a manner as the nasal mucus, which comes out of the nose, draws the nasal mucus inside the nose.

Consequently, according to the present invention, the nasal mucus is removed as the absorbing member 300 moves forward and rearward and rotates simultaneously in a state in which the absorbing member 300 is coupled spirally, and as a result, it is possible to remove the nasal mucus from the target person without irritation because artificial suction force is not used.

Further, the rotary aspirator may minimize the occurrence of injuries to a mucous membrane inside the nose, a blood vessel, or a periphery of a nostril because the rotary aspirator uses surface viscosity of nasal mucus, the rotary aspirator is environmentally friendly because a separate power source is not used, and the rotary aspirator may be used semipermanently because the absorbing member 300 may be changed and used.

While the specific exemplary embodiments related with the rotary aspirator according to the present invention have been described above, the exemplary embodiments may be modified to various exemplary embodiments without departing from the scope of the present invention.

Therefore, the scope of the present invention should not be limited to the described exemplary embodiment, but should be defined by the appended claims and the equivalents of the claims.

Accordingly, it should be understood that the aforementioned exemplary embodiments are described for illustration in all aspects and are not limited, and the scope of the present invention shall be represented by the claims to be described below, instead of the detailed description, and it should be construed that all of the changes or modified forms induced from the meaning and the scope of the claims, and an equivalent concept thereto are included in the scope of the present invention.

The invention claimed is:

1. A rotary aspirator comprising:
a body portion which has a length in a front and rear direction, and has an outer circumferential surface formed as any one of a circular shape, an elliptical shape, and a polygonal shape in a lateral direction;
a handle which is connected to a rear end of the body portion and has a smaller diameter than the rear end of the body portion so that a user moves the handle forward and rearward and rotates the handle in a state in which the user holds the handle by hand; and an absorbing member which is provided on the body portion and is configured to absorb nasal mucus of a target person, wherein a coupling hole into which one end or both ends of the absorbing member is/are inserted is penetratively formed in the body portion in the lateral direction.

2. The rotary aspirator of claim 1, wherein a front end of the body portion is formed to protrude in a hemispheric shape.

3. The rotary aspirator of claim 1, wherein the coupling hole is opened to a front side of the body portion so that the absorbing member is coupled through the front side of the body portion.

4. The rotary aspirator of claim 3, wherein the coupling hole is formed to have a width narrower than the absorbing member, and holds an outer surface of the absorbing member.

5. The rotary aspirator of claim 1, wherein a catching protrusion for catching and positioning the absorbing member is formed to protrude on an outer surface of the body portion in a longitudinal direction.

6. The rotary aspirator of claim 1, wherein a catching protrusion or a catching groove for catching and positioning the absorbing member is concavely formed at an upper surface or a lower surface of the coupling hole.

7. The rotary aspirator of claim 1, wherein the absorbing member is attached to the outer circumferential surface of the body portion by an adhesive.

8. The rotary aspirator of claim 1, wherein the absorbing member is continuously and spirally wound in the front and rear direction of the body portion.

9. The rotary aspirator of claim 1, wherein a diameter of the body portion is gradually decreased forward.

* * * * *